(12) United States Patent
Do et al.

(10) Patent No.: US 12,402,867 B2
(45) Date of Patent: Sep. 2, 2025

(54) HEMOSTATIC BIOPSY TRACT ARTICLE

(71) Applicant: C.R. Bard, Inc., Franklin Lakes, NJ (US)

(72) Inventors: Hiep Do, Chandler, AZ (US); Jordan Addison, Gilbert, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 926 days.

(21) Appl. No.: 17/428,797

(22) PCT Filed: Feb. 15, 2019

(86) PCT No.: PCT/US2019/018292
§ 371 (c)(1),
(2) Date: Aug. 5, 2021

(87) PCT Pub. No.: WO2020/167319
PCT Pub. Date: Aug. 20, 2020

(65) Prior Publication Data
US 2022/0000459 A1    Jan. 6, 2022

(51) Int. Cl.
| | |
|---|---|
| A61B 90/00 | (2016.01) |
| A61B 10/02 | (2006.01) |
| A61L 31/04 | (2006.01) |
| A61L 31/14 | (2006.01) |
| C08L 1/28 | (2006.01) |

(Continued)

(52) U.S. Cl.
CPC .......... *A61B 10/0275* (2013.01); *A61B 90/39* (2016.02); *A61L 31/041* (2013.01); *A61L 31/146* (2013.01); *A61L 31/148* (2013.01); *C08L 1/286* (2013.01); *C08L 3/04* (2013.01); *C08L 5/08* (2013.01); *A61B 2090/3908* (2016.02); *A61L 2400/04* (2013.01)

(58) Field of Classification Search
None
See application file for complete search history.

(56) References Cited

U.S. PATENT DOCUMENTS

| | | | |
|---|---|---|---|
| 6,056,970 A | 5/2000 | Greenawalt et al. | |
| 6,060,461 A | 5/2000 | Drake | |
| 6,270,464 B1 | 8/2001 | Fulton et al. | |

(Continued)

FOREIGN PATENT DOCUMENTS

| | | |
|---|---|---|
| CN | 101001649 A | 7/2007 |
| CN | 101485897 A | 7/2009 |

(Continued)

OTHER PUBLICATIONS

Chinese Office Action and Search Report dated Mar. 22, 2022 pertaining to Chinese patent application 201980092012.2.

(Continued)

*Primary Examiner* — Nicole P Babson
(74) *Attorney, Agent, or Firm* — DINSMORE & SHOHL LLP

(57) ABSTRACT

A hemostatic biopsy tract article includes a bioresorbable body having a microporous structure. The bioresorbable body is formed by a mixture that includes a bioabsorbable hemostatic powder, a hydrolyzed starch, hyaluronic acid, and carboxymethylcellulose. Optionally, a marker element may be coupled to the bioresorbable body, wherein the marker element is formed from a material that is imageable under at least one imaging modality.

15 Claims, 2 Drawing Sheets

(51) Int. Cl.
*C08L 3/04* (2006.01)
*C08L 5/08* (2006.01)

(56) References Cited

U.S. PATENT DOCUMENTS

| | | | |
|---|---|---|---|
| 6,356,782 B1 | 3/2002 | Sirimanne et al. | |
| 6,394,965 B1 | 5/2002 | Klein | |
| 6,846,320 B2 | 1/2005 | Ashby et al. | |
| 7,329,414 B2 | 2/2008 | Fisher et al. | |
| 7,744,852 B2 | 6/2010 | Chernomorsky et al. | |
| 8,320,993 B2 | 11/2012 | Sirimanne et al. | |
| 8,401,622 B2 | 3/2013 | Talpade et al. | |
| 8,880,154 B2 | 11/2014 | Jones et al. | |
| 9,044,162 B2 | 6/2015 | Jones et al. | |
| 9,149,341 B2 | 10/2015 | Jones et al. | |
| 9,327,061 B2 | 5/2016 | Govil et al. | |
| 9,801,688 B2 | 10/2017 | Jones et al. | |
| 9,820,824 B2 | 11/2017 | Jones et al. | |
| 2002/0016612 A1* | 2/2002 | Ashby | A61B 17/0057 606/213 |
| 2002/0035324 A1 | 3/2002 | Sirimanne et al. | |
| 2005/0142161 A1 | 6/2005 | Freeman et al. | |
| 2007/0065484 A1 | 3/2007 | Chudzik et al. | |
| 2007/0086958 A1 | 4/2007 | Drake et al. | |
| 2007/0087061 A1 | 4/2007 | Drake et al. | |
| 2009/0062233 A1 | 3/2009 | Ji | |
| 2010/0082102 A1 | 4/2010 | Govil et al. | |
| 2010/0179589 A1 | 7/2010 | Roorda et al. | |
| 2011/0144661 A1 | 6/2011 | Houser et al. | |
| 2012/0143243 A1 | 6/2012 | Hill et al. | |
| 2013/0245680 A1 | 9/2013 | Sargeant et al. | |
| 2014/0171385 A1 | 6/2014 | Burbank et al. | |
| 2015/0119907 A1 | 4/2015 | Fenton et al. | |
| 2015/0289861 A1 | 10/2015 | Macphee et al. | |
| 2016/0015475 A1 | 1/2016 | Jones et al. | |
| 2017/0216499 A1 | 8/2017 | Kaplan | |

FOREIGN PATENT DOCUMENTS

| | | |
|---|---|---|
| CN | 101977561 A | 2/2011 |
| CN | 102056564 A | 5/2011 |
| CN | 103687631 A | 3/2014 |
| CN | 104353130 A | 2/2015 |
| CN | 104665897 A | 6/2015 |
| CN | 104888264 A | 9/2015 |
| CN | 204683720 U | 10/2015 |
| CN | 105194712 A | 12/2015 |
| GB | 2281861 | 11/1993 |
| JP | 2002513645 A | 5/2002 |
| JP | 2009508653 A | 3/2009 |
| WO | 2006005340 A1 | 1/2006 |
| WO | 2009091549 A1 | 7/2009 |
| WO | 2009105177 A1 | 8/2009 |
| WO | 2009134314 A1 | 11/2009 |
| WO | 2013003045 A2 | 1/2013 |

OTHER PUBLICATIONS

Chinese Second Office Action and Search Report dated Nov. 18, 2022, pertaining to Chinese patent application 201980092012.2.
Japanese Office Action dated Nov. 28, 2022, pertaining to Japanese patent application 2021-547357.

* cited by examiner

HEMOSTATIC BIOPSY TRACT ARTICLE

CROSS-REFERENCE TO RELATED APPLICATIONS

This application is a U.S. national phase of International Application No. PCT/US2019/018292, filed Feb. 15, 2019, which is incorporated herein by reference in its entirety.

TECHNICAL FIELD

The present invention relates a biopsy article for use in biopsy procedures, and, more particularly, to a biopsy tract article having hemostatic properties.

BACKGROUND ART

A stereotactic biopsy procedure is performed by inserting a biopsy probe, e.g., needle, into a patient to form a tract to the biopsy site, where the biopsy probe collects one or more biopsy samples and forms a cavity as a result of tissue removal. Such a biopsy procedure typically results in significant bleeding at the tract, which may include the biopsy cavity, well after the biopsy has been completed. Also, after most biopsies, a tissue marker is deployed at the biopsy site to mark the location of the biopsy site. The tissue marker is configured to be visible under one or more imaging modalities, such as for example, ultrasound, MRI and X-ray.

What is needed in the art is a hemostatic biopsy tract article that may serve as a hemostatic tract plug, and which optionally may carry a tissue marker so as to both mark the biopsy site and effectively control bleeding at the biopsy site.

SUMMARY OF INVENTION

The present invention provides a hemostatic biopsy tract article that may serve as a hemostatic tract plug, and which optionally may carry a tissue marker so as to both mark the biopsy site and effectively control bleeding at the biopsy site.

The invention in one form is directed to a hemostatic biopsy tract article. The hemostatic biopsy tract article includes a bioresorbable body having a microporous structure. The bioresorbable body is formed by a mixture that includes a bioabsorbable hemostatic powder, a hydrolyzed starch, hyaluronic acid, and carboxymethylcellulose. Optionally, a marker element may be coupled to the bioresorbable body, wherein the marker element is formed from a material that is imageable under at least one imaging modality.

One advantage of the invention is that the bioresorbable body instantly dehydrates and gels blood upon contact with blood by the effect of its hydrophilic materials and microporous structure.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
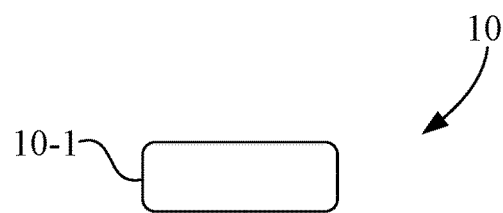
FIG. 1 is a side view of a hemostatic biopsy tract article having a bioresorbable body with a microporous structure.

Referring now to the drawings, and more particularly to FIG. 1, there is shown a hemostatic biopsy tract article 10 in accordance with the present invention.

Figure 2:
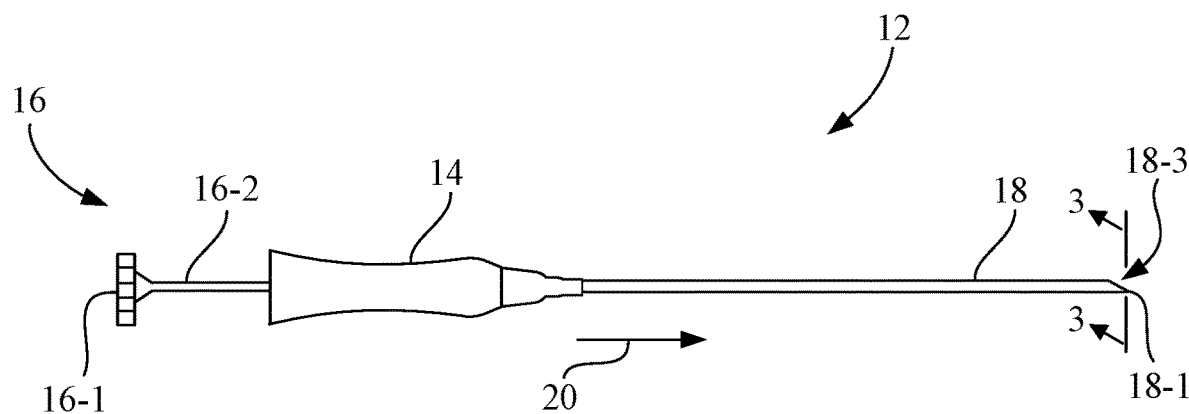
FIG. 2 is a side view of an introducer device for carrying and delivering the hemostatic biopsy tract article of FIG. 1.

Referring also to FIG. 2, hemostatic biopsy tract article 10 is designed to be carried by, and expelled from, an introducer device 12. In the present embodiment, hemostatic biopsy tract article 10 has an elongate cylindrical shape, although it is contemplated that other shapes may be selected, for example, based on the application for which hemostatic biopsy tract article 10 is to be used. Introducer device 12 includes a handle body 14, a plunger 16, and a cannula 18. In the present embodiment, handle body 14 is molded to cannula 18.

Figure 3:
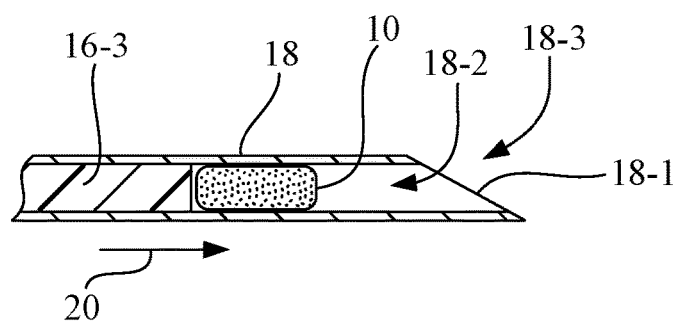
FIG. 3 is a section view of a distal portion of the introducer device of FIG. 2 taken along line 3-3 of FIG. 2.

Referring also to FIG. 3, cannula 18 includes a distal end 18-1 and a lumen 18-2. Lumen 18-2 distally terminates at distal end 18-1 to define a delivery port 18-3 associated with lumen 18-2. Plunger 16 includes a plunger head 16-1 and a plunger shaft 16-2 that extends from plunger head 16-1. A distal portion 16-3 of plunger shaft 16-2 of plunger 16 is slidably received in lumen 18-2 of cannula 18. Hemostatic biopsy tract article 10 is positioned in lumen 18-2 of cannula 18 distal to distal portion 16-3 of plunger 16.

By depressing plunger head 16-1 in a distal direction 20, plunger shaft 16-2 moves in distal direction 20 so as to expel hemostatic biopsy tract article 10 from delivery port 18-3 of cannula 18.

Those skilled in the art will recognize that the distal end 18-1 of cannula 18 may have a configuration other than the beveled tip configuration as shown. For example, it is contemplated that distal end 18-1 may be blunt, rounded, symmetrically pointed, asymmetrically pointed, etc. Also, as an alternative to delivery port 18-3 being located at distal end 18-1 of cannula 18, it is contemplated that delivery port 18-3 may be formed in the side wall of cannula 18 to facilitate a side delivery of hemostatic biopsy tract article 10 from cannula 18.

Hemostatic biopsy tract article 10 is configured such that bioresorbable body 10-1 is bioresorbable, hemostatic, and has a microporous structure. In the present embodiment, bioresorbable body 10-1 is formed by a mixture, e.g., a solution, which includes a bioabsorbable hemostatic powder, a hydrolyzed starch, hyaluronic acid, and carboxymethylcellulose. Each of the bioabsorbable hemostatic powder, the hydrolyzed starch, the hyaluronic acid, and the carboxymethylcellulose is a hydrophilic material, and thus, in the present embodiment, bioresorbable body 10-1 is formed using four different hydrophilic materials.

The bioabsorbable hemostatic powder is a plant-based starch powder of a different starch material from that of the hydrolyzed starch. The bioabsorbable hemostatic powder may be, for example, an unhydrolyzed starch. In one form, the bioabsorbable hemostatic powder is commercially available under the tradename, Arista(™) from C. R. Bard, Inc. (See, e.g., U.S. Pat. No. 6,060,461). The Arista brand starch is an unhydrolyzed starch (plant-based) that comprises of large number of glucose units. In contrast to the Arista brand starch, the hydrolyzed starch contains shorter glucose units (e.g. monosaccharides, disaccharides or trisaccharides).

Hydrolyzed starch consists of smaller saccharides molecules than an initial starch. Starch is a polymeric carbohydrate consisting of a large number of glucose units joined by glycoside bonds. Whenever starch (polysaccharides) molecules undergo hydrolysis, it forms either monosaccharides, disaccharides or trisaccharides.

Hyaluronic acid is an anionic, nonsulfated glycosaminoglycan, which are long unbranched polysaccharides consisting of a repeating disaccharide unit.

Carboxymethylcellulose (CMC) is a cellulose derivative with carboxymethyl groups bound to some of the hydroxyl groups of the glucopyranose monomers that make up the cellulose backbone.

Where the mixture is a solution containing water, e.g., distilled water, the mixture is lyophilized or compressed to remove the water and form bioresorbable body 10-1. In the present embodiment, no other ingredients are added in this solution. However, it is contemplated that drugs or growth factors can be incorporated in the solution to generate foam that can deliver bioactive components, if desired.

In one example, to achieve the microporous structure having hemostatic and bioresorbable characteristics of the present invention, a ratio of hyaluronic acid to carboxymethylcellulose is in a range of 1:1 to 4:1, and a ratio of the bioabsorbable hemostatic powder to the hydrolyzed starch is in a range of 1:1 to 3:1. It has been observed that a pore size of bioresorbable body 10-1 may be increased by increasing the ratio of hyaluronic acid to carboxymethylcellulose. Conversely, a pore size of the bioresorbable body 10-1 may be decreased by decreasing the ratio of hyaluronic acid to carboxymethylcellulose.

In one embodiment, hemostatic biopsy tract article 10 is formed from a solution that includes the bioabsorbable hemostatic powder (4% to 7% by weight/volume), the hydrolyzed starch (2% to 4% by weight/volume), the hyaluronic acid (0.3% to 1.3% by weight/volume), and the carboxymethylcellulose (0.3% to 1.3% by weight/volume). The estimated overall pore size range is from 20 nanometers to as large as 5 microns.

A specific example follows below.

EXAMPLE: In the present example, a bioresorbable body having a microporous structure in accordance with the present invention is formed by making a solution that is formed by dissolving in distilled water: bioabsorbable hemostatic powder, e.g. Arista brand starch powder, (5% by weight/volume), hydrolyzed starch (4% by weight/volume), hyaluronic acid (0.313% by weight/volume), and carboxymethylcellulose (0.626% by weight/volume). The solution is mixed for 15 minutes or until all particles are dissolved, and is then poured into an open-top container which is then placed onto a pre-cooled shelf, and the microporous foam is formed by removing water by a sublimation process or freeze drying process (e.g., the entire process takes about 24 hours). The pore size of the microporous foam of this example is in a range of 20 nanometers to about 5 microns.

Advantageously, bioresorbable body 10-1 of hemostatic biopsy tract article 10 instantly dehydrates and gels blood upon contact with blood by the effect of the hydrophilic materials and microporous structure. Also, hemostatic biopsy tract article 10 is completely resorbed over a period of time, with the bioabsorbable hemostatic powder being resorbed within 24 to 48 hours of amylases. Again, the bioabsorbable hemostatic powder is a plant-based starch powder of a different starch material from that of the hydrolyzed starch.

It is contemplated that bioresorbable body 10-1 of hemostatic biopsy tract article 10 may be placed into any biopsy tract to achieve hemostasis following a biopsy. Such biopsies may include, for example, a breast biopsy or an organ biopsy, such as for example, a liver or renal biopsy. Further, it is contemplated that lung biopsies may also be embolized with bioresorbable body 10-1 of hemostatic biopsy tract article 10 to form a blood clot at the pleural surfaces and prevent a pneumothorax and promote tissue re-modeling of the lung parenchyma once a blood clot is formed.

Figures 4A, 4B:
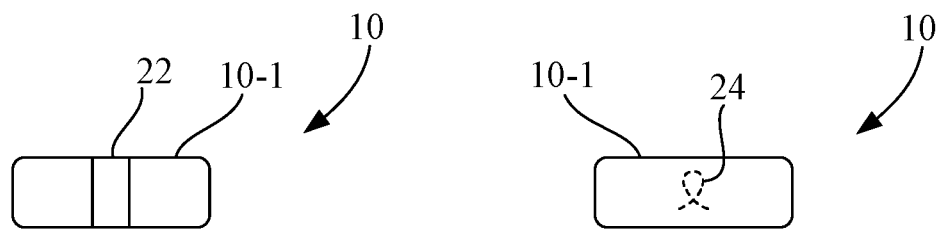
FIG. 4A is a side view of the hemostatic biopsy tract article having a tissue marker attached to the bioresorbable body.
FIG. 4B is a side view of the hemostatic biopsy tract article having a tissue marker contained in the bioresorbable body.

Referring to the embodiments of FIGS. 4A and 4B, hemostatic biopsy tract article 10 may be adapted to include a tissue marker formed from a material that is imageable under at least one imaging modality, e.g., x-ray, MRI, or ultrasound.

For example, as depicted in FIG. 4A, hemostatic biopsy tract article 10 may be adapted to include a marker element 22 that is coupled to bioresorbable body 10-1. Marker element 22 is formed from a material that is imageable under at least one imaging modality, e.g., x-ray, MRI, or ultrasound. For example, where the desired imaging modality is x-ray or MRI, marker element 22 may be formed from stainless steel or titanium. Where the desired imaging modality is ultrasound, marker element 22 may be formed to include reflective surfaces. In the present embodiment depicted in FIG. 4A, marker element 22 is an exterior band attached to an exterior of bioresorbable body 10-1.

In the example depicted in FIG. 4B, hemostatic biopsy tract article 10 may be adapted to contain a marker element 24, which in turn is coupled to bioresorbable body 10-1 by being contained within bioresorbable body 10-1. Marker element 24 is formed from a material that is imageable under at least one imaging modality, e.g., x-ray, MRI, or ultrasound. For example, where the desired imaging modality is x-ray or MRI, marker element 24 may be formed from stainless steel or titanium. Where the desired imaging modality is ultrasound, marker element 24 may be formed to include reflective surfaces. In the present embodiment depicted in FIG. 4B, marker element 24 has a ribbon shape, but it is to be recognized that other shapes of marker element 24, e.g., ring, flat, coil, loop, hook, polygonal, spherical, elliptical, star, ribbon, a combination, etc., may be utilized based on the medical application or user preference.

While in the embodiments set forth above, bioresorbable body 10-1 of hemostatic biopsy tract article 10 is depicted as having an elongate cylindrical shape, it is contemplated that other shapes may be selected, for example, based on the application for which hemostatic biopsy tract article 10 is to be used. For example, it is contemplated that bioresorbable body 10-1 of hemostatic biopsy tract article 10 could also be a rolled flat sheet, or multiple flat sheets, and may include a radiopaque or other imageable marker element embedded in the sheet or between sheets.

Figure 5:
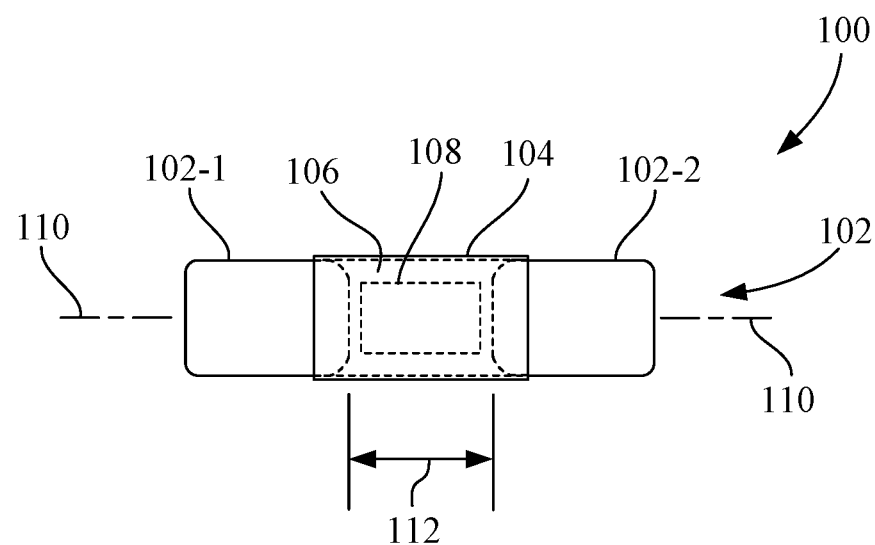
FIG. 5 is a side view of another embodiment of a hemostatic biopsy tract article that includes a bioresorbable body having a first body segment separated from a second body segment to define a void that carries a marker element, with the void being encapsulated by a bioresorbable sleeve.

FIG. 5 shows an embodiment of a hemostatic biopsy tract article 100, in accordance with another embodiment of the invention. Hemostatic biopsy tract article 100 may be used to mark a biopsy cavity and/or tract, such as for example, a breast biopsy cavity where tissue samples have been removed.

Hemostatic biopsy tract article 100 includes a bioresorbable body 102, a bioresorbable sleeve 104, a void 106, and a marker element 108. In the present embodiment, hemostatic biopsy tract article 10 has an elongate cylindrical shape, and also may be carried and delivered by an introducer device, such as introducer device 12 shown in FIG. 2.

Bioresorbable body 102 includes a first body segment 102-1 and a second body segment 102-2. First body segment 102-1 and a second body segment 102-2 are arranged along a longitudinal axis 110. First body segment 102-1 is spaced a distance 112 from second body segment 102-2 along longitudinal axis 110 to form the void 106 between first body segment 102-1 and second body segment 102-2. Marker element 108 is positioned in void 106 between first body segment 102-1 and second body segment 102-2. Bioresorbable sleeve 104 encapsulates void 106 to contain marker element 108, and bioresorbable sleeve 104 connects, e.g., by a friction fit or biocompatible adhesive, to each of first body segment 102-1 and second body segment 102-2.

Bioresorbable body 102 has the same chemical composition as that of bioresorbable body 10-1 described above. Accordingly, each of first body segment 102-1 and a second body segment 102-2 also has the same chemical composition as that of bioresorbable body 10-1 described above. First body segment 102-1 and a second body segment 102-2 may be formed individually, or separated from the same base bioresorbable body, such as for example, by dividing bioresorbable body 10-1 into two body segments.

Bioresorbable sleeve 104 may have the same chemical composition as that of bioresorbable body 10-1, described above, or alternatively, may be a tube formed from another type of bioresorbable material.

Void 106 may be an air space, or alternatively, may be filled with a biocompatible fluid, such as saline or an MRI contrast agent.

Marker element 108 is formed from a material that is imageable under at least one imaging modality, e.g., x-ray, MRI, or ultrasound. Marker element 108 is shown schematically as a rectangle, but may be any suitable shape as determined or desired for a particular purpose. For example, the shape of marker element 108 may be a ring, flat, coil, loop, hook, polygonal, spherical, elliptical, star, ribbon, a combination, etc. Where the desired imaging modality is x-ray or MRI, marker element 108 may be formed from stainless steel or titanium. Where the desired imaging modality is ultrasound, marker element 108 may be formed to include reflective surfaces. It is noted that void 106 may itself provide ultrasound and MRI contrast. Also, it is contemplated that marker element 108 may itself be a plurality of individual marker elements.

As used herein, the terms "connected" or "attached" mean a direct or indirect affixation of one component to another component. The term "about", and other words of degree, are relative modifiers intended to indicate permissible variation from the characteristic so modified.

The following items also relate to the invention:

A hemostatic biopsy tract article includes a bioresorbable body having a microporous structure. The bioresorbable body may be formed by a mixture that includes a bioabsorbable hemostatic powder, a hydrolyzed starch, hyaluronic acid, and carboxymethylcellulose.

Optionally, a ratio of hyaluronic acid to carboxymethylcellulose may be in a range of 1:1 to 4:1.

Optionally, a ratio of the bioabsorbable hemostatic powder to the hydrolyzed starch may be in a range of 1:1 to 3:1.

A pore size of the bioresorbable body may be increased by increasing the ratio of hyaluronic acid to carboxymethylcellulose and/or the pore size is in a range of 20 nanometers to 5 microns.

A pore size of the bioresorbable body may be decreased by decreasing the ratio of hyaluronic acid to carboxymethylcellulose and/or the pore size is in a range of 20 nanometers to 5 microns.

Optionally, the mixture may be a solution containing water, and wherein the mixture may be lyophilized or compressed to remove the water and form the bioresorbable body.

Optionally, the mixture may be a solution that includes the bioabsorbable hemostatic powder (4% to 7% by weight/volume), the hydrolyzed starch (2% to 4% by weight/volume), the hyaluronic acid (0.3% to 1.3% by weight/volume), and the carboxymethylcellulose (0.3% to 1.3% by weight/volume).

In at least one embodiment, the bioresorbable body is configured such that it instantly dehydrates and gels blood upon contact with blood.

In at least one embodiment, the bioresorbable body is configured such that it is completely resorbed over a period of time.

Optionally, the bioabsorbable hemostatic powder may be a plant-based starch powder, and/or is of a different starch material than the hydrolyzed starch.

Optionally, a marker element may be coupled to the bioresorbable body. The marker element may be formed from a material that is imageable under at least one imaging modality.

Optionally, the marker element may be attached to the bioresorbable body.

Optionally, alternatively or additionally, the marker element may be contained within the bioresorbable body.

In another optional arrangement, the bioresorbable body may have a longitudinal axis, a first body segment, and a second body segment, wherein the first body segment is spaced from the second body segment along the longitudinal axis to form a void between the first body segment and the second body segment. Optionally, the marker element is positioned in the void between the first body segment and the second body segment. A bioresorbable sleeve may encapsulate the void and connect to each of the first body segment and the second body segment.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A hemostatic biopsy tract article, comprising a bioresorbable body having a microporous structure, the bioresorbable body being formed by a mixture that includes a bioabsorbable hemostatic powder in an amount of 4% to 7% by weight/volume, wherein the bioresorbable hemostatic powder is an unhydrolyzed, plant-based starch, a hydrolyzed starch in an amount of 2% to 4% by weight/volume, hyaluronic acid in an amount of 0.3% to 1.3% by weight/volume, and carboxymethylcellulose in an amount of 0.3% to 1.3% by weight/volume and water, wherein the microporous structure has a pore size from 20 nanometers to 5 microns, wherein the microporous structure is formed by removing water by a sublimation or freeze-drying process.

2. The hemostatic biopsy tract article according to claim 1, wherein a ratio of hyaluronic acid to carboxymethylcellulose is in a range of 1:1 to 4:1.

3. The hemostatic biopsy tract article according to claim 1, wherein a ratio of the bioabsorbable hemostatic powder to the hydrolyzed starch is in a range of 1:1 to 3:1.

4. The hemostatic biopsy tract article according to claim 2, wherein a ratio of the bioabsorbable hemostatic powder to the hydrolyzed starch is in a range of 1:1 to 3:1.

5. The hemostatic biopsy tract article according to claim 1, wherein the pore size of the bioresorbable body is increased by increasing a ratio of hyaluronic acid to carboxymethylcellulose.

6. The hemostatic biopsy tract article according to claim 1, wherein the pore size of the bioresorbable body is decreased by decreasing a ratio of hyaluronic acid to carboxymethylcellulose.

7. The hemostatic biopsy tract article according to claim 2, wherein the pore size of the bioresorbable body is increased by increasing the ratio of hyaluronic acid to carboxymethylcellulose.

8. The hemostatic biopsy tract article according to claim 2, wherein the pore size of the bioresorbable body is decreased by decreasing the ratio of hyaluronic acid to carboxymethylcellulose.

9. The hemostatic biopsy tract article according to claim 1, wherein the bioresorbable body instantly dehydrates and gels blood upon contact with blood.

10. The hemostatic biopsy tract article according to claim 2, wherein the bioresorbable body instantly dehydrates and gels blood upon contact with blood.

11. The hemostatic biopsy tract article according to claim 1, wherein the bioresorbable body is completely resorbed over a period of time.

12. The hemostatic biopsy tract article according to claim 1, comprising a marker element coupled to the bioresorbable body, the marker element being formed from a material that is imageable under at least one imaging modality.

13. The hemostatic biopsy tract article according to claim 12, wherein the marker element is attached to the bioresorbable body.

14. The hemostatic biopsy tract article according to claim 12, wherein the marker element is contained within the bioresorbable body.

15. The hemostatic biopsy tract article according to claim 12, wherein:
the bioresorbable body has a longitudinal axis, a first body segment, and a second body segment, the first body segment being spaced from the second body segment along the longitudinal axis to form a void between the first body segment and the second body segment, the marker element being positioned in the void between the first body segment and the second body segment, and further comprising:
a bioresorbable sleeve that encapsulates the void and connects to each of the first body segment and the second body segment.

* * * * *